(12) United States Patent
Tanaka et al.

(10) Patent No.: US 9,351,949 B2
(45) Date of Patent: May 31, 2016

(54) PROPHYLACTIC/THERAPEUTIC AGENT FOR INFLUENZA VIRUS INFECTION (71) Applicants: SBI PHARMACEUTICALS CO., LTD., Minato-ku, Tokyo (JP); Tokushima University, Tokushima-shi, Tokushima (JP)

(72) Inventors: Tohru Tanaka, Tokyo (JP); Motowo Nakajima, Tokyo (JP); Kiwamu Takahashi, Tokyo (JP); Takuya Ishii, Tokyo (JP); Hiroshi Kido, Tokushima (JP); Junji Chida, Tokushima (JP); Kazuhiko Yamane, Tokushima (JP)

(73) Assignees: SBI Pharmaceuticals Co., Ltd., Tokyo (JP); Tokushima University, Tokushima (JP)

( * ) Notice: Subject to any disclaimer, the term of this patent is extended or adjusted under 35 U.S.C. 154(b) by 0 days.

(21) Appl. No.: 14/414,578

(22) PCT Filed: Jun. 3, 2013

(86) PCT No.: PCT/JP2013/003486
§ 371 (c)(1),
(2) Date: Jan. 13, 2015

(87) PCT Pub. No.: WO2014/013664
PCT Pub. Date: Jan. 23, 2014

(65) Prior Publication Data
US 2015/0164838 A1    Jun. 18, 2015

(30) Foreign Application Priority Data

Jul. 19, 2012  (JP) .................................. 2012-160999

(51) Int. Cl.
*A61K 31/197*    (2006.01)
*A61K 33/26*    (2006.01)
(Continued)

(52) U.S. Cl.
CPC ............. *A61K 31/197* (2013.01); *A61K 31/194* (2013.01); *A61K 33/26* (2013.01); *A61K 45/06* (2013.01)

(58) Field of Classification Search
None
See application file for complete search history.

(56) References Cited

U.S. PATENT DOCUMENTS

| 8,563,605 B2 | 10/2013 | Miyanari et al. |
| 2001/0053796 A1 | 12/2001 | Kim et al. |

(Continued)

FOREIGN PATENT DOCUMENTS

| CN | 101874795 A | 11/2010 |
| CN | 102461733 A | 5/2012 |

(Continued)

OTHER PUBLICATIONS

"Antiviral Agents" in Kirk-Othmer Encyclopedia of Chemical Technology; Ramachandra S. Hosmane, Published Online: Jun. 20, 2003, Copyright © 2001 by John Wiley & Sons, Inc., pp. 135-182.*

(Continued)

*Primary Examiner* — Karl J Puttlitz
(74) *Attorney, Agent, or Firm* — Foley & Lardner LLP (57) ABSTRACT

Provided is a prophylactic/therapeutic agent for influenza viral infection that is effective not only before and at an early stage of infection with influenza virus but also at an intermediate or late stage of the infection and is highly safe for human bodies. A prophylactic/therapeutic drug for influenza viral infection comprising, as active ingredients, 5-aminolevulinic acid (5-ALA), a derivative thereof or a salt of the 5-ALA or the derivative, and an iron compound is prepared. This prophylactic/therapeutic agent can be used for ameliorating (preventing) depression in food consumption, water consumption and body weight, for ameliorating (decreasing) increase in ketone body levels in blood that may otherwise cause ketosis, for ameliorating (preventing) depression in ATP levels in blood, or for ameliorating (increasing) a survival rate and depression in a body surface temperature.

8 Claims, 4 Drawing Sheets

(51) Int. Cl.
*A61K 31/194* (2006.01)
*A61K 45/06* (2006.01)

(56) References Cited

U.S. PATENT DOCUMENTS

| | | |
|---|---|---|
| 2004/0234555 A1 | 11/2004 | Oshida et al. |
| 2008/0026075 A1 | 1/2008 | Kondo et al. |
| 2010/0120916 A1 | 5/2010 | Kuroiwa et al. |
| 2011/0196033 A1 | 8/2011 | Tanaka |
| 2015/0174090 A1 | 6/2015 | Tanaka et al. |

FOREIGN PATENT DOCUMENTS

| | | |
|---|---|---|
| JP | 2000-510123 A | 8/2000 |
| JP | 2001299381 * | 10/2001 |
| JP | 2001-316255 A | 11/2001 |
| JP | 2006-096746 A | 4/2006 |
| JP | 2009-143939 A | 7/2009 |
| JP | 2011-016753 A | 1/2011 |
| WO | WO 97/41855 A1 | 11/1997 |
| WO | WO 2009/139156 A1 | 11/2009 |
| WO | WO 2010/050179 A1 | 5/2010 |
| WO | WO 2014/010206 A1 | 1/2014 |

OTHER PUBLICATIONS

Machine Translation of JP 2001299381.*
Obuchi, Miyako, "Ketone body (in blood; in urine)," Tonyobyo Care, 2010, 7(1):22-26, with partial English translation.
Iwai et al., "Anti-Influenza Activity of Marchantins, Macrocyclic Bisbibenzyls Contained in Liverworts," PLOS ONE, May 2011, 6(5):E19825:1-11.

* cited by examiner

PROPHYLACTIC/THERAPEUTIC AGENT FOR INFLUENZA VIRUS INFECTION

CROSS-REFERENCE TO RELATED APPLICATIONS

This application is a National Stage application of PCT/JP2013/003486, filed Jun. 3, 2013, which claims priority from Japanese application JP 2012-160999, filed Jul. 19, 2012.

TECHNICAL FIELD

The present invention relates to a prophylactic and/or therapeutic agent for influenza viral infection, and more particularly, it relates to a prophylactic and/or therapeutic agent for influenza viral infection comprising 5-aminolevulinic acid (5-ALA), a derivative thereof or a salt of the 5-ALA or the derivative, and an iron compound.

BACKGROUND ART

Influenza viral infection prevailing on a worldwide scale every year causes mass infection including fatal cases. Although effectiveness of administration of an anti-influenza virus drug at an initial stage of the viral infection has been proved, the effect is reduced by half if timing of the administration is misjudged. As therapeutic drugs for influenza viral infection currently clinically used for the treatment of influenza, oseltamivir and zanamivir that inhibit the action of neuraminidase, that is, an enzyme present on the surface of influenza virus, amantadine that inhibits M2 protein of influenza virus, ribavirin of a nucleotide drug, and influenza vaccines utilizing immunity are known. There are a few drugs that are effective for influenza viral infection and have a high degree of safety, and in addition, appearance of viruses resistant to these drugs has started to be regarded as a problem, and therefore, a novel prophylactic/therapeutic drug for influenza viral infection is expected to be developed.

On the other hand, 5-ALA is known as an intermediate of a tetrapyrrole biosynthetic pathway widely present in animals, plants and fungi, and is generally biosynthesized by a 5-aminolevulinic acid synthetase from succinyl CoA and glycine. Photodynamic therapy or photokinetic therapy using the 5-ALA (hereinafter also referred to as the "ALA-PDT") has been developed and attracts attention as a low invasive therapy in which QOL may be retained, and diagnostic/therapeutic agents or the like using ALAs or the like for a tumor have been reported. It is also known that the 5-ALA is useful as a preventing/ameliorating agent or a therapeutic agent for adult diseases, cancers and male sterility (see, for example, Patent Documents 1 to 3).

PRIOR ART DOCUMENTS

Patent Documents

[Patent Document 1] International Publication No. WO2010/050179
[Patent Document 2] Japanese unexamined Patent Application Publication No. 2011-16753
[Patent Document 3] International Publication No. WO2009/139156

SUMMARY OF THE INVENTION

Object to be Solved by the Invention

The timing for attaining effectiveness of the conventional therapeutic drugs for influenza viral infection is limited to an early stage (within 48 hours) of the infection, and the site of action of the therapeutic drugs for influenza viral infection is in inhibition of multiplication of the virus, and hence the drugs are not effective for energy metabolism insufficiency of vascular endothelial cells that occurs at an intermediate or late stage of the infection and may bring on aggravation such as ketosis. It is reported that a fatality rate was 50% even in cases of early administration of within 4 days when an anti-influenza virus drug was used for cases of infection with virulent H5N1 in Hong Kong. An object of the present invention is to provide a prophylactic/therapeutic agent for influenza viral infection that is effective not only before and at an early stage of infection with influenza virus but also at an intermediate or late stage of the infection and is highly safe for human bodies.

Means to Solve the Object

A treatment for influenza viral infection employed today is performed principally by administering an anti-influenza virus drug for inhibiting the multiplication of the virus within a body, but this treatment is not effective unless the drug is administered at an early stage within 48 hours after the infection. Particularly when an infant or an old person is affected by influenza, aggravated cases of not only influenza-associated encephalopathy but also of crisis of critical ketosis caused by multiple organ failure have been reported. It has become clear through recent studies that one of factors of such aggravation is energy metabolism insufficiency of vascular endothelial cells and this energy metabolism insufficiency causes aggravation from peripheral circulation failure to the multiple organ failure. However, the currently effective treatment is merely the administration of an anti-influenza virus drug at an early stage of the infection as described above, and there is no safe therapeutic drug capable of inhibiting the energy metabolism insufficiency occurring at an intermediate or late stage of the infection. The present inventors came up with an idea that the aggravation of influenza derived from failure in the body energy metabolism may be prevented by administration of 5-ALA and an iron compound, and by actually using model mice for aggravation of influenza, have found the following: Depression in food consumption, water consumption, body weight and body temperature derived from influenza viral infection can be thus prevented so as to avoid the aggravation of influenza, resulting in ameliorating increase in ketone body levels in blood, ameliorating depression in ATP levels in blood, ameliorating a survival rate and ameliorating abnormality in the body surface temperature, and thus, the present invention has been accomplished.

Specifically, the present invention relates to: [1] a prophylactic and/or therapeutic agent for influenza viral infection comprising a compound represented by the following formula (I) or a salt thereof:

(wherein $R^1$ represents a hydrogen atom or an acyl group, and $R^2$ represents a hydrogen atom, a linear or branched alkyl group, a cycloalkyl group, an aryl group or an aralkyl group); [2] the prophylactic and/or therapeutic agent for influenza viral infection according to [1], wherein $R^1$ and $R^2$ each represent a hydrogen atom; [3] the prophylactic and/or therapeutic agent for influenza viral infection according to [1] or [2], further comprising an iron compound; [4] the prophylactic and/or therapeutic agent for influenza viral infection according to [3], wherein the iron compound is one or more compounds selected from ferric chloride, iron sesquioxide, iron sulfate, ferrous pyrophosphate, ferrous citrate, iron sodium citrate, sodium ferrous citrate, iron ammonium citrate, ferric pyrophosphate, iron lactate, ferrous gluconate, iron sodium diethylenetriaminepentaacetate, iron ammonium diethylenetriaminepentaacetate, iron sodium ethylenediamine tetraacetate, iron ammonium ethylenediamine tetraacetate, iron sodium dicarboxymethyl glutamate, iron ammonium dicarboxymethyl glutamate, ferrous fumarate, iron acetate, iron oxalate, ferrous succinate, sodium iron succinate citrate, heme iron, iron dextran, iron triethylenetetramine, lactoferrin iron, transferrin iron, sodium iron chlorophyllin, ferritin iron, saccharated iron oxide and iron glycine sulfide; [5] the prophylactic and/or therapeutic agent for influenza viral infection according to [3], wherein the iron compound is sodium ferrous citrate; [6] the prophylactic and/or therapeutic agent for influenza viral infection according to any one of [1] to [5], wherein the prophylactic and/or therapeutic agent is used for ameliorating depression in food consumption, water consumption and/or body weight; [7] the prophylactic and/or therapeutic agent for influenza viral infection according to any one of [1] to [6], wherein the prophylactic and/or therapeutic agent is used for ameliorating increase in ketone body levels in blood and/or depression in ATP levels in blood; and [8] the prophylactic and/or therapeutic agent for influenza viral infection according to any one of [1] to [7], wherein the prophylactic and/or therapeutic agent is used for ameliorating depression in a survival rate and/or abnormality in a body surface temperature. Other aspects of these inventions relating to the prophylactic and/or therapeutic agent for influenza viral infection include a compound represented by the above formula (I) or a salt thereof for preventing and/or treating influenza viral infection and a compound represented by the above formula (I) or a salt thereof for use in prevention and/or treatment of influenza viral infection.

Furthermore, the present invention relates to [9] a prophylactic and/or therapeutic method for influenza viral infection, comprising administering to a subject the prophylactic and/or therapeutic agent for influenza viral infection according to any one of [1] to [8]; [10] a prophylactic and/or therapeutic kit for influenza viral infection comprising a) a compound represented by the above formula (I) or a salt thereof (wherein $R^1$ represents a hydrogen atom or an acyl group, and $R^2$ represents a hydrogen atom, a linear or branched alkyl group, a cycloalkyl group, an aryl group or an aralkyl group), and b) an iron compound; and [11] a prophylactic and/or therapeutic method for influenza viral infection, comprising administering to a subject a) a compound represented by the above formula (I) or a salt thereof (wherein $R^1$ represents a hydrogen atom or an acyl group, and $R^2$ represents a hydrogen atom, a linear or branched alkyl group, a cycloalkyl group, an aryl group or an aralkyl group), and b) an iron compound, simultaneously or one after another.

Moreover, the present invention relates to [12] a combination of prophylactic and/or therapeutic agents, comprising a) the prophylactic and/or therapeutic agent for influenza viral infection according to any one of [1] to [8]; and b) an anti-influenza drug; and [13] a combination of prophylactic and/or therapeutic agents, comprising a) a compound represented by the above formula (I) or a salt thereof (wherein $R^1$ represents a hydrogen atom or an acyl group, and $R^2$ represents a hydrogen atom, a linear or branched alkyl group, a cycloalkyl group, an aryl group or an aralkyl group), b) an iron compound, and c) an anti-influenza drug.

Furthermore, the present invention relates to [14] an agent for suppressing increase in ketone body levels in blood comprising a compound represented by the above formula (I) or a salt thereof (wherein $R^1$ represents a hydrogen atom or an acyl group, and $R^2$ represents a hydrogen atom, a linear or branched alkyl group, a cycloalkyl group, an aryl group or an aralkyl group). Other aspects of this invention include a method for suppressing increase in ketone body levels in blood in which a compound represented by the above formula (I) or a salt thereof is administered to a subject; and a compound represented by the above formula (I) or a salt thereof used for suppressing increase in ketone body levels in blood.

Effect of the Invention

The present invention can provide a highly safe prophylactic and/or therapeutic agent for influenza viral infection that improves a survival rate by preventing depression in food consumption, water consumption, body weight and body temperature of a subject for avoiding aggravation of influenza as well as an agent for suppressing increase in ketone body levels in blood.

MODE OF CARRYING OUT THE INVENTION

A prophylactic and/or therapeutic agent for influenza viral infection of the present invention is not especially limited as long as it is an agent comprising, as an active ingredient, a compound represented by the above formula (I) or a salt thereof (hereinafter, sometimes generically designated as "ALAs"), and the agent preferably contains an iron compound in addition to the ALAs, and more preferably, the agent is one usable for ameliorating (preventing) depression in food consumption, water consumption and/or body weight, for ameliorating (decreasing) increase in ketone body levels in blood that may otherwise cause the ketosis, for ameliorating (preventing) depression in ATP levels in blood, and for ameliorating (increasing) a survival rate and/or abnormality in a body surface temperature. A prophylactic and/or therapeutic method for influenza viral infection of the present invention comprises administering the aforementioned prophylactic and/or therapeutic agent for influenza viral infection of the present invention to a subject such as a human, a domestic animal, a domestic fowl or a pet.

Furthermore, a prophylactic and/or therapeutic kit for influenza viral infection of the present invention is not especially limited as long as it is a kit individually comprising, as active ingredients, ALAs and an iron compound, and preferably, the kit is one usable for ameliorating (preventing) depression in food consumption, water consumption and/or body weight, for ameliorating (decreasing) increase in ketone body levels in blood that may otherwise cause the ketosis, for ameliorating (preventing) depression in ATP levels in blood, and for ameliorating (increasing) a survival rate and/or abnormality in a body surface temperature. Thus, the kit of the present invention is limited to a use as a prophylactic and/or therapeutic kit for influenza viral infection. The prophylactic and/or therapeutic kit for influenza viral infection of the present invention generally comprises a component usually used in such a type of prophylactic and/or therapeutic kit, such as a carrier, a pH buffer or a stabilizer, as well as an accompanying document such as an instruction sheet. A prophylactic and/or therapeutic method for influenza viral infection of the present invention using this prophylactic and/or therapeutic kit for influenza viral infection of the present invention comprises administering ALAs and an iron compound simultaneously or one after another to a subject such as a human, a domestic animal, a domestic fowl or a pet.

Furthermore, a combination of prophylactic and/or therapeutic agents of the present invention is not especially limited as long as it is a prophylactic/therapeutic drug combination of the aforementioned prophylactic and/or therapeutic agent for influenza viral infection of the present invention and an anti-influenza drug, or a prophylactic/therapeutic drug combination of ALAs, an iron compound and an anti-influenza drug, and influenza viral infection can be prevented and/or treated also by administering such a prophylactic/therapeutic drug combination. These combined pharmaceutics (components) can be simultaneously or individually administered.

Furthermore, an agent for suppressing increase in ketone body levels in blood of the present invention is not especially limited as long as it comprises ALAs as an active ingredient, and the agent preferably contains an iron compound in addition to the ALAs. Alternatively, a kit for suppressing increase in ketone body levels in blood can be realized by individually comprising ALAs and an iron compound as active ingredients. Such a kit generally comprises a component usually used in such a type of kit, such as a carrier, a pH buffer or a stabilizer, as well as an accompanying document such as an instruction sheet. The agent for suppressing increase in ketone body levels in blood can be administered to a subject, or the ALAs and the iron compound can be administered simultaneously or one after another to a subject such as a human, a domestic animal, a domestic fowl or a pet using the kit for suppressing increase in ketone body levels in blood, to thereby suppress the increase in ketone body levels in blood.

Preferable examples of ALAs include 5-ALA, which is a compound of formula (I) wherein $R^1$ and $R^2$ are both a hydrogen atom, or a salt thereof. The 5-ALA is a kind of amino acid also designated as δ-aminolevulinic acid. Examples of the derivative of the 5-ALA include compounds of formula (I), other than the 5-ALA, wherein $R^1$ is a hydrogen atom or an acyl group, and $R^2$ is a hydrogen atom, a linear or branched alkyl group, a cycloalkyl group, an aryl group or an aralkyl group.

Examples of the acyl group in formula (I) include linear or branched alkanoyl groups having 1 to 8 carbon atoms, such as a formyl group, an acetyl group, a propionyl group, a butyryl group, an isobutyryl group, a valeryl group, an isovaleryl group, a pivaloyl group, a hexanoyl group, an octanoyl group and a benzylcarbonyl group, and aroyl groups having 7 to 14 carbon atoms such as a benzoyl group, a 1-naphthoyl group and a 2-naphthoyl group.

Examples of the alkyl group in formula (I) include linear or branched alkyl groups having 1 to 8 carbon atoms, such as a methyl group, an ethyl group, a propyl group, an isopropyl group, a butyl group, an isobutyl group, a sec-butyl group, a tert-butyl group, a pentyl group, an isopentyl group, a neopentyl group, a hexyl group, a heptyl group and an octyl group.

Examples of the cycloalkyl group in formula (I) include saturated or optionally partially unsaturated cycloalkyl groups having 3 to 8 carbon atoms, such as a cyclopropyl group, a cyclobutyl group, a cyclopentyl group, a cyclohexyl group, a cycloheptyl group, a cyclooctyl group, a cyclododecyl group and a 1-cyclohexenyl group.

Examples of the aryl group in formula (I) include aryl groups having 6 to 14 carbon atoms, such as a phenyl group, a naphthyl group, an anthryl group and a phenanthryl group.

As for the aralkyl group in formula (I), examples of an aryl portion are the same as those of the aryl group mentioned above, examples of an alkyl portion are the same as those of the alkyl group mentioned above, and specific examples of the aralkyl group include aralkyl groups having 7 to 15 carbon atoms, such as a benzyl group, a phenethyl group, a phenylpropyl group, a phenylbutyl group, a benzhydryl group, a trityl group, a naphthylmethyl group and a naphthylethyl group.

The ALA derivative is preferably compounds of formula (I) wherein $R^1$ is a formyl group, an acetyl group, a propionyl group, a butyryl group, or the like, or compounds of formula (I) wherein $R^2$ is a methyl group, an ethyl group, a propyl group, a butyl group, a pentyl group, or the like, and preferable examples of a combination of $R^1$ and $R^2$ include combinations of a formyl group and a methyl group, an acetyl group and a methyl group, a propionyl group and a methyl group, a butyryl group and a methyl group, a formyl group and an ethyl group, an acetyl group and an ethyl group, a propionyl group and an ethyl group, and a butyryl group and an ethyl group.

The ALAs may act as an active ingredient in an organism in the form of the 5-ALA of formula (I) or the derivative thereof, and may be administered, in accordance with the administration form, as various salts for increasing solubility, an ester or a prodrug (precursor) to be degraded by an enzyme in an organism. Examples of salts of the 5-ALA and the derivative thereof include pharmacologically acceptable acid addition salts, metal salts, ammonium salts and organic amine addition salts. Examples of the acid addition salts include various inorganic acid salts such as hydrochloride, hydrobromide, hydroiodide, phosphate, nitrate and sulfate, and various organic acid addition salts such as formate, acetate, propionate, toluenesulfonate, succinate, oxalate, lactate, tartrate, glycolate, methanesulfonate, butyrate, valerianate, citrate, fumarate, maleate and malate. Examples of the metal salts include alkali metal salts such as a lithium salt, a sodium salt and a potassium salt, alkali earth metal salts such as a magnesium salt and a calcium salt, and metal salts such as an aluminum salt and a zinc salt. Examples of the ammonium salts include an ammonium salt and an alkyl ammonium salt such as a tetramethyl ammonium salt. Examples of the organic amine salts include a triethylamine salt, a piperidine salt, a morpholine salt and a toluidine salt. It is noted that such a salt may be in the form of a solution at the time of use.

Among these ALAs, preferable are 5-ALA, various esters such as 5-ALA methyl ester, 5-ALA ethyl ester, 5-ALA propyl ester, 5-ALA butyl ester and 5-ALA pentyl ester, and hydrochlorides, phosphates and sulfates of these, and among them 5-ALA hydrochloride or 5-ALA phosphate is particularly preferable.

These ALAs may be produced by any of known methods of chemical synthesis, microbial production and enzymatic production. Furthermore, the ALAs may be in the form of a hydrate or a solvate, and one of these ALAs may be singly used or two or more of them may be appropriately combined for use.

The iron compound may be an organic salt or an inorganic salt, and examples of the inorganic salt include ferric chloride, iron sesquioxide, iron sulfate and ferrous pyrophosphate, and examples of the organic salt include carboxylates, for example, citrates that are hydroxy carboxylates, such as ferrous citrate, iron sodium citrate, sodium ferrous citrate and iron ammonium citrate; organic acid salts such as ferric pyrophosphate, iron lactate, ferrous gluconate, iron sodium diethylenetriamine pentaacetate, iron ammonium diethylenetriamine pentaacetate, iron sodium ethylenediamine tetraacetate, iron ammonium ethylenediamine tetraacetate, iron sodium dicarboxymethyl glutamate, iron ammonium dicarboxymethyl glutamate, ferrous fumarate, iron acetate, iron oxalate, ferrous succinate and sodium iron succinate citrate; heme iron, iron dextran, iron triethylenetetramine, lactoferrin iron, transferrin iron, sodium iron chlorophyllin, ferritin iron, saccharated iron oxide and iron glycine sulfide, of which sodium ferrous citrate and iron sodium citrate are preferred.

One of the aforementioned iron compounds may be singly used or a mixture of two or more of them may be used. A dose of the iron compound may be in a molar ratio of 0.01 to 100, preferably 0.05 to 10 and more preferably 0.1 to 8 based on a dose of the ALAs (in terms of the 5-ALA).

In the prophylactic and/or therapeutic method for influenza viral infection of the present invention, a composition comprising ALAs and the iron compound may be administered, or ALAs and the iron compound may be individually administered simultaneously or one after another. If they are individually administered, they are preferably administered simultaneously. If they are individually administered one after another, they are administered preferably without a considerable interval, so that the administration of ALAs and the iron compound may exhibit an additive effect, preferably a synergistic effect.

The prophylactic and/or therapeutic agent for influenza viral infection or the prophylactic and/or therapeutic kit for influenza viral infection of the present invention can be used in combination further with one or more anti-influenza drugs such as oseltamivir, zanamivir, amantadine, peramivir, laninamivir and favipiravir. Since the prophylactic and/or therapeutic agent for influenza viral infection and the prophylactic and/or therapeutic kit for influenza viral infection of the present invention are different from these existing anti-influenza drugs in the mechanism of action, when the combination with the prophylactic and/or therapeutic agent for influenza viral infection of the present invention is employed, an additive effect, or a synergistic effect in certain cases, can be expected.

An example of a method for suppressing increase in ketone body levels in blood includes a method in which a composition comprising ALAs and the iron compound is administered or ALAs and the iron compound are individually administered simultaneously or one after another. If they are individually administered, they are preferably administered simultaneously. If they are individually administered one after another, they are administered preferably without a considerable interval, so that the administration of ALAs and the iron compound may exhibit an additive effect, preferably a synergistic effect.

As the route of administration of the prophylactic and/or therapeutic agent for influenza viral infection, the respective components of the prophylactic and/or therapeutic kit, the respective components of the combination of the prophylactic/therapeutic agents, the agent for suppressing increase in ketone body levels in blood or the respective components of the increase suppression kit of the present invention, oral administration including sublingual administration, and parenteral administration such as nasal administration, inhalation administration, intravenous administration including drip, dermal administration with a cataplasm, a suppository or administration by forced enteral nutrition using a nasogastric tube, a nasoenteric tube, a gastrostomy tube or an enterostomy tube may be employed. Incidentally, as the route of administration of an anti-influenza drug used in the combination of the prophylactic/therapeutic agents, a route of administration already accepted for the drug is preferably employed.

The dosage form of the prophylactic and/or therapeutic agent for influenza viral infection, the respective components of the prophylactic and/or therapeutic kit, the agent for suppressing increase in ketone body levels in blood or the respective components of the increase suppression kit of the present invention can be appropriately determined in accordance with the route of administration, and examples of the dosage form include an injection, nasal drops, drops, a tablet, a capsule, a subtle granule, a powder, a solution, a solution dissolved in a syrup or the like, a cataplasm and a suppository. The prophylactic and/or therapeutic agent for influenza viral infection, the respective components of the prophylactic and/or therapeutic kit, the agent for suppressing increase in ketone body levels in blood or the respective components of the increase suppression kit of the present invention can be used not only as a medicine but also as a supplement in the form of a tablet or a capsule. Furthermore, especially for an old person or an infant having difficulty in swallowing, a form of a disintegrating tablet that may be rapidly disintegrated in a mouth or a form of a solution suitable to administration with a nasogastric tube is preferably employed.

In order to prepare the prophylactic and/or therapeutic agent for influenza viral infection, the prophylactic and/or therapeutic kit, the agent for suppressing increase in ketone body levels in blood or the increase suppression kit of the present invention, pharmacologically acceptable carrier, filler, diluent, additive, disintegrator, binder, coating, lubricant, slipping agent, lubricating agent, flavoring agent, sweetener, solubilizer, solvent, gelling agent, nutrient and the like can be added if necessary, and specific examples of such additional components include water, saline, animal fat and oil, vegetable oil, lactose, starch, gelatin, crystalline cellulose, gum, talc, magnesium stearate, hydroxypropyl cellulose, polyalkylene glycol, polyvinyl alcohol and glycerin.

Incidentally, if the prophylactic agent for influenza viral infection of the present invention is prepared as an aqueous solution, it is necessary to pay attention not to make the aqueous solution alkaline so that degradation of ALAs can be prevented, and if the aqueous solution unavoidably becomes alkaline, the degradation can be prevented by removing oxygen.

The prophylactic and/or therapeutic agent for influenza viral infection, the prophylactic and/or therapeutic kit, the agent for suppressing increase in ketone body levels in blood or the increase suppression kit of the present invention can be used not only for a human but also in the veterinary field for a domestic animal, a domestic fowl, a pet and the like. If the subject is a human, the dose and the administration frequency and period of the prophylactic and/or therapeutic agent or the like depends upon the age, the body weight, the symptom of the patient infected with influenza virus, and the dose of the ALAs can be, in terms of moles of the ALAs, 0.01 mmol to 25 mmol/day, preferably 0.025 mmol to 7.5 mmol/day, more preferably 0.075 mmol to 5.5 mmol/day, still more preferably 0.2 mmol to 2 mmol/day and particularly preferably 0.45 mmol to 1.3 mmol/day per adult, and the administration frequency can be one to several doses per day or continuous administration in drips or the like. The administration period can be determined by a pharmacologist or a clinician of the relevant technical field by a known method, and at the time of determination, ketone body levels in blood or ATP levels in blood can be used as an index.

The present invention will now be more specifically described with reference to examples, and it is noted that the technical scope of the present invention is not limited to these examples.

EXAMPLES

Example 1

The influence of administration of 5-ALA hydrochloride and sodium ferrous citrate on a body weight, food consumption, water consumption and biochemical parameters were examined by using model mice for aggravation of influenza. Specifically, an effect of the administration of ALA+Fe to suppress phenomena, caused in accordance with the progress of the disease state of mice infected with and affected by influenza virus, of depression in water consumption and food consumption and a shift from glucose metabolism to fat metabolism was verified.

[Experimental Method]

(1) Animals and Breeding Conditions

Female C57BL/6J mice were purchased at 4 weeks old from Japan SLC, Inc., and mice found to be healthy by visual examination on the day of receipt were used for tests. On the next day of receipt, the mice were divided by random sampling into three groups each of ten mice on the basis of their body weights, and each group was further divided into three groups respectively of three mice, three mice and four mice per cage. The mice were allowed to freely take a basic feed MF manufactured by Oriental Yeast Co., Ltd. and tap water, and were bred in a breeding facility having a room temperature of 23 to 24° C. and humidity of 30 to 40% and lighted by a fluorescent lamp for 12 hours.

(2) Test Groups

The mice were divided into three groups 1) to 3) different in viral infection and administered drugs as follows:

Group 1): group noninfected with the virus (orally administered with CMC): ten mice Group 2): group infected with the virus (orally administered with CMC): ten mice Group 3): group infected with the virus and administered with ALA+Fe: ten mice (3) Influenza Viral Infection Under anesthesia with Ketalar and Selactar, a solution of influenza virus PR8 strain was given to the lung of each mouse through both nasal cavities. The viral load was 100 PFU per mouse. The day of infection with the virus was set as Day-0.

(4) Administration of Agents

At 10:00 AM and 17:00 PM every day, the mice of the groups 1) and 2) were forcedly administered intragastrically with 0.1 mL of a methyl cellulose solution (0.5 w/v %, Methyl Cellulose 400 cP Solution, Sterilized: Wako Pure Chemical Industries, Ltd.) by using a probe, and the mice of the group 3) were forcedly administered intragastrically, by using a probe, with 0.1 mL of a solution prepared by dissolving 5-ALA hydrochloride and sodium ferrous citrate in a methyl cellulose solution immediately before the administration. A dose of the 5-ALA hydrochloride for the group 3) was 15 mg per kg of the body weight of each mouse and was 30 mg per kg per day. Besides, a dose of the sodium ferrous citrate was 23.54 mg per kg of the body weight of each mouse, which corresponds to a molar ratio of 0.5 on the basis of the dose of the 5-ALA hydrochloride, and was 47.08 mg per kg per day.

(5) Body Weight, Food Consumption and Water Consumption

The respective cages were observed every day, and the body weight of each mouse and the food consumption and the water consumption of each cage were measured before administering the agent at 10:00 AM.

(6) Dissection and Biochemical Test

On Day-4 and Day-7, five mice each were dissected. Blood was collected by decapitating each mouse under no anesthesia for performing a biochemical blood test (for ketone body levels). A measurement kit of "Precision Xceed 3-hydroxybutyric acid kit (manufactured by Abbott Japan Co., Ltd.)" was used for measuring ketone body levels in blood.

[Results]

(1) Change in Body Weight

Figure 1:
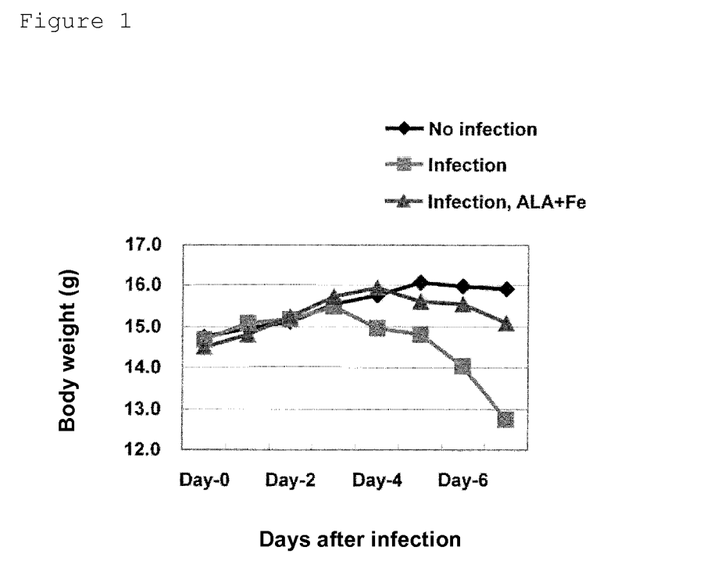
FIG. 1 is a diagram illustrating change in body weight caused by administering 5-ALA and sodium ferrous citrate of the present invention to model mice for aggravation of influenza.

The change in body weight of the test groups used in the test is illustrated in FIG. 1. The group 1) noninfected with the virus, the group 2) infected with the virus and the group 3) infected with the virus and administered with ALA+Fe all showed similar body weight gain up to Day-3. However, abrupt weight depression was observed in the group 2) infected with the virus from Day-4, and weight depression of approximately 20% as compared with the body weight on Day-3 was observed on Day-7, the final day of the observation. On the other hand, the group 1) noninfected with the virus showed weight gain up to Day-5, and thereafter, the body weight was retained until Day-7, the final day of the observation. The group 3) infected with the virus and administered with ALA+Fe showed body weight gain up to Day-4, and thereafter, showed gradual body weight depression until Day-7. The body weight depression on Day-7, the final day of the observation, was, however, merely approximately 6% as compared with the body weight on Day-4.

(2) Change in Food Consumption

Figure 2:
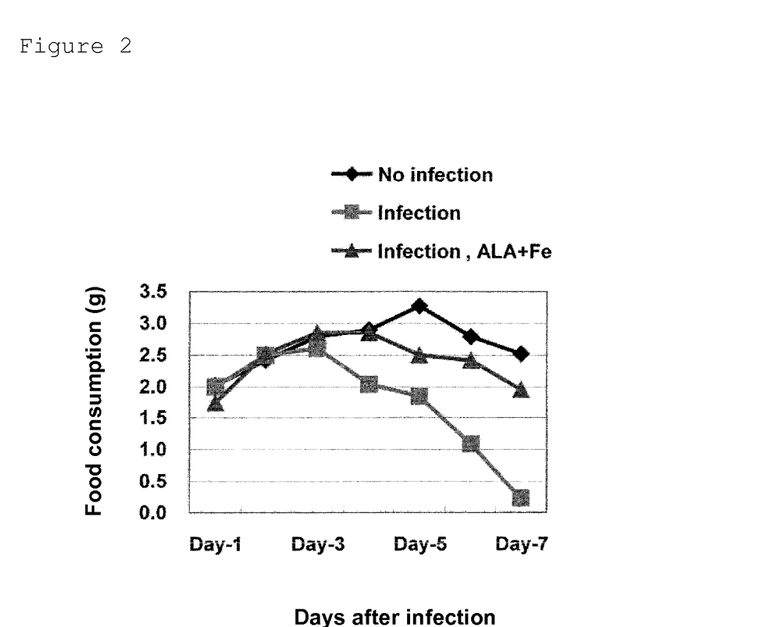
FIG. 2 is a diagram illustrating change in food consumption caused by administering 5-ALA and sodium ferrous citrate of the present invention to model mice for aggravation of influenza.

The change in food consumption of the test groups used in the test is illustrated in FIG. 2. The group 1) noninfected with the virus, the group 2) infected with the virus and the group 3) infected with the virus and administered with ALA+Fe all showed similar increase in the food consumption up to Day-2. With respect to the group 2) infected with the virus, however, the increasing rate of the food consumption showed tendency to stop increasing as compared with the other two groups on Day-3, and abrupt depression in the food consumption was observed from Day-4. On Day-7, the final day of the observation, the depression in the food consumption of approximately 90% as compared with the food consumption on Day-3 was observed. On the other hand, the group 1) noninfected with the virus showed increase in the food consumption up to Day-5. The group 3) infected with the virus and administered with ALA+Fe showed increase in the food consumption up to Day-4, and thereafter, showed gradual depression until Day-7. The depression in the food consumption on Day-7, the final day of the observation, was, however, merely approximately 35% as compared with the food consumption on Day-4.

(3) Change in Water Consumption

Figure 3:
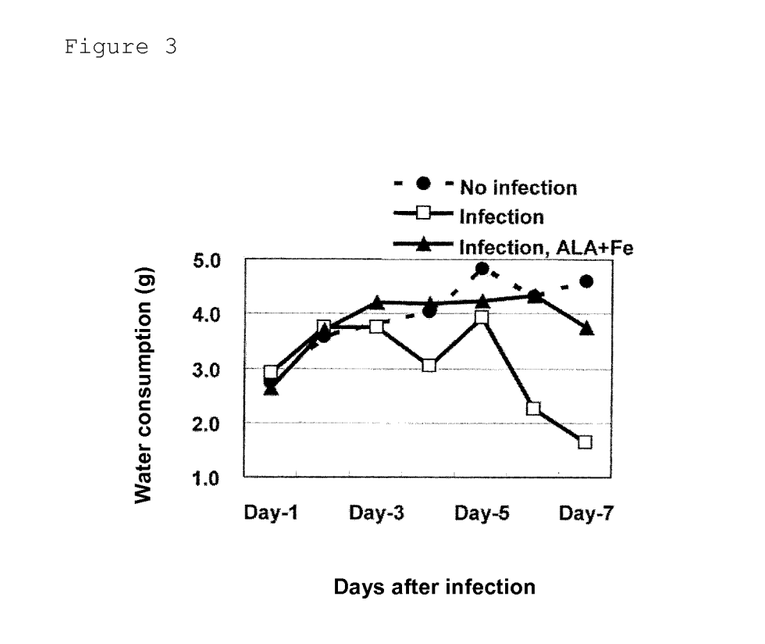
FIG. 3 is a diagram illustrating change in water consumption caused by administering 5-ALA and sodium ferrous citrate of the present invention to model mice for aggravation of influenza.

The change in water consumption of the test groups used for the test is illustrated in FIG. 3. With respect to the group 2) infected with the virus, increase in the water consumption was stopped before Day-2, and the water consumption was depressed once on Day-4. Although the water consumption was recovered once on Day-5, it was abruptly depressed thereafter. On Day-7, the final day of the observation, depression in the water consumption of approximately 60% as compared with the water consumption on Day-3 was observed. With respect to the group 3) infected with the virus and administered with ALA+Fe, increase in the water consumption was observed up to Day-6, and gradual depression was observed on Day-7, but the depression in the water consumption was merely approximately 12% as compared with the water consumption on Day-6.

(4) Change in Ketone Body Levels in Blood

Figure 4:
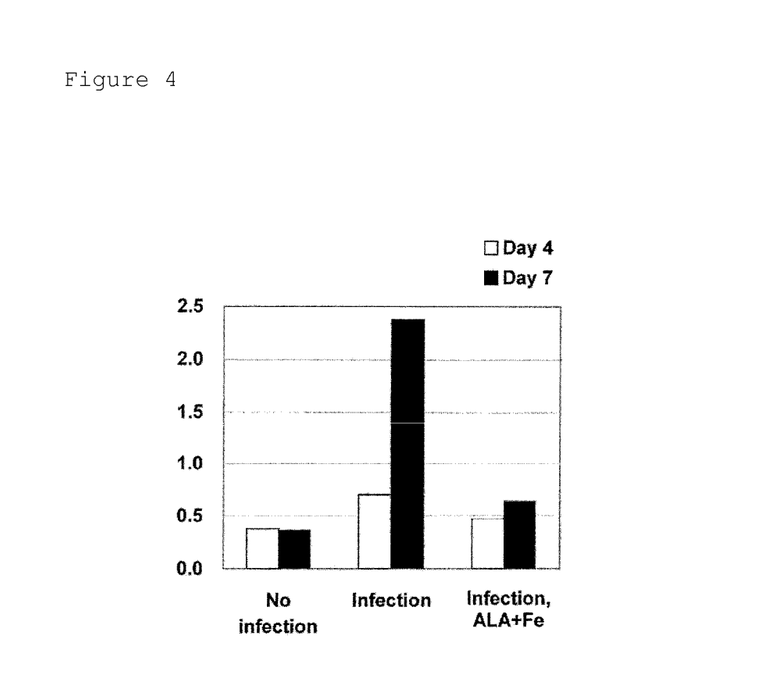
FIG. 4 is a diagram illustrating change in ketone body levels in blood caused by administering 5-ALA and sodium ferrous citrate of the present invention to model mice for aggravation of influenza.

The change in ketone body levels in blood of the test groups used in the test is illustrated in FIG. 4. The value of ketone body levels in blood obtained on Day-7 was, as compared with that obtained on Day-4, not changed with respect to the group 1) noninfected with the virus, increased by merely 25% with respect to the group 3) infected with the virus and administered with ALA+Fe, and greatly increased by 242% with respect to the group 2) infected with the virus.

Example 2

Influence of the administration of 5-ALA hydrochloride and sodium ferrous citrate on a survival rate and a body surface temperature was examined by using model mice for aggravation of influenza. Specifically, it was verified whether or not the effect, observed in Example 1, of the administration of ALA+Fe to suppress the phenomena, caused in the model mice for aggravation of influenza, of depression in water consumption, food consumption and body weight and increase in ketone levels in blood would affect a survival rate and a body temperature of mice as well as the ATP levels in blood.

[Experimental Method]

(1) Animals, Breeding Conditions, Test Groups and Administration of Drugs

Animals, breeding conditions, test groups and administration of drugs employed in this example were the same as those of Example 1.

(2) Influenza Viral Infection

Under anesthesia with Ketalar and Selactar, a solution of influenza virus PR8 strain of fresh virus obtained immediately after egg culture and showing a high fatality rate was given to the lung of each mouse through both nasal cavities (among various experimental virus strains, the PR8 is a strain with the highest fatality rate, and a virus strain obtained immediately after the culture shows particularly strong pathogenicity). The viral load was 100 PFU or 150 PFU per mouse. The day of infection with the virus was set as Day-0.

(3) Measurement of Survival Rate and Body Surface Temperature

Each cage was observed every day, and a ratio of the number of survivors to the total number of mice was calculated as a survival rate. Furthermore, the body surface temperature of each survivor was measured at 17:00 on and after Day-6.

(4) Dissection and Biochemical Test

On Day-4 and Day-7, five mice each were dissected. Blood was collected by decapitating each mouse under no anesthesia for performing a biochemical blood test (for ATP levels). A measurement kit of "XL-ATP kit (manufactured by APRO Science Inc.)" was used for the measurement of ATP levels in blood.

[Results]

(1) Transition of Survival Rate

Figure 5:
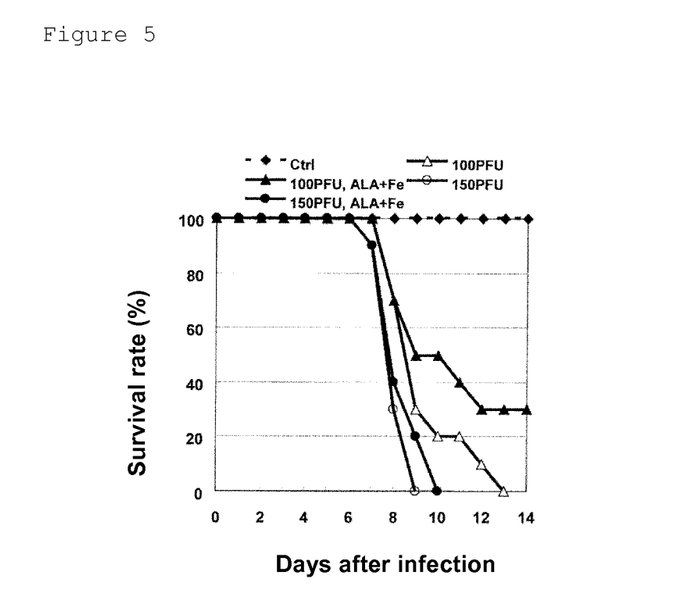
FIG. 5 is a diagram illustrating transition of a survival rate (under infection conditions where an aggravation rate is high) obtained in administering 5-ALA and sodium ferrous citrate of the present invention to model mice for aggravation of influenza.

The transition of the survival rate is illustrated in FIG. 5. In the case of the infection with a viral load of 150 PFU, all the mice died by Day-9 in the group 2) infected with the virus and not administered with ALA, and by Day-10 in the group 3) infected with the virus and administered with ALA+Fe. In the case of the infection with a viral load of 100 PFU, the survival rate was varied on and after Day-9 depending upon whether or not the ALA was administered, and all the mice died before Day-13 in the group 2) infected with the virus and not administered with the ALA, but three mice survived the test in the group 3) infected with the virus and administered with ALA+Fe. This result reveals that the survival rate is improved even when the influenza virus PR8 strain showing a high fatality rate is used.

(2) Transition of Body Temperature

Figure 6:
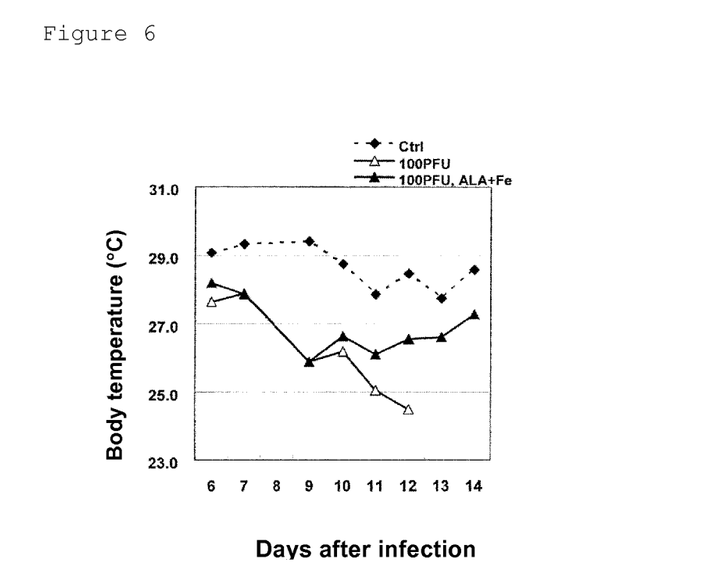
FIG. 6 is a diagram illustrating transition of a body surface temperature obtained in administering 5-ALA and sodium ferrous citrate of the present invention to model mice for aggravation of influenza.

The transition of the body surface temperature of the survivor mice is illustrated in FIG. 6. In the group 2) infected with the virus and not administered with ALA, the body temperature continuously dropped after the infection. As for the dead mice, they died on the next day following temperature drop to the level of 24° C. On the other hand, in the group 3) infected with the virus and administered with ALA+Fe, the body temperature was gradually recovered on and after Day-9. It is thus understood that the abnormality in the body surface temperature can be improved by administering ALA+Fe.

(3) Change in ATP Levels in Blood

Figure 7:
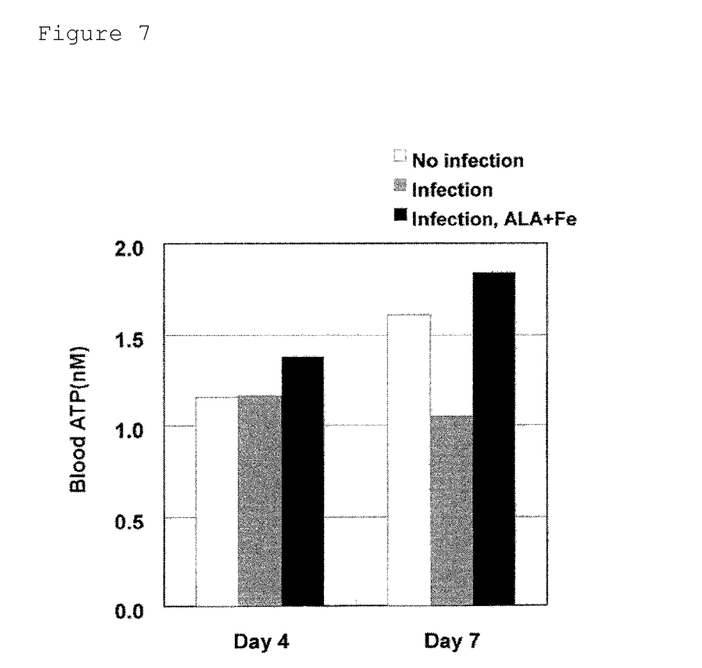
FIG. 7 is a diagram illustrating change in ATP levels in blood caused by administering 5-ALA and sodium ferrous citrate of the present invention to model mice for aggravation of influenza.

The change in ATP levels in blood of the test groups used in the test obtained on Day-4 and Day-7 is illustrated in FIG. 7. ATP levels in blood obtained on Day-7 of the group 2) infected with the virus had a value smaller than that of the group 1) noninfected with the virus. On the other hand, the ATP levels in blood obtained on Day-7 of the group 3) infected with the virus and administered with ALA+Fe was not lowered and had a large value even on Day-7. Besides, the value of ATP levels in blood was increased as compared with that obtained on Day-4.

Reference Example

Next, a survival rate of model mice for aggravation of influenza infected with influenza virus PR8 strain with low pathogenicity was examined. Specifically, instead of the influenza virus PR8 strain, used in Example 2, of fresh virus obtained immediately after egg culture and showing a high fatality rate, influenza virus PR8 strain that had been stored, after the culture, under a condition of −80° C. for 3 to 6 months so as to lose the high fatality rate was used for examining a survival rate.

Mice were divided into test groups of a group 1) noninfected with the virus and a group 2) infected with the virus, and the test was performed in the same manner as in Example 2 by employing the same conditions of the animals, the breeding conditions, influenza viral infection and the administration of drug except that the influenza virus PR8 strain not having a high fatality rate as compared with the influenza virus PR8 strain used in Example 2 was used. Furthermore, each cage was observed every day, and a ratio of the number of survivors to the total number of mice was calculated as a survival rate.

Figure 8:
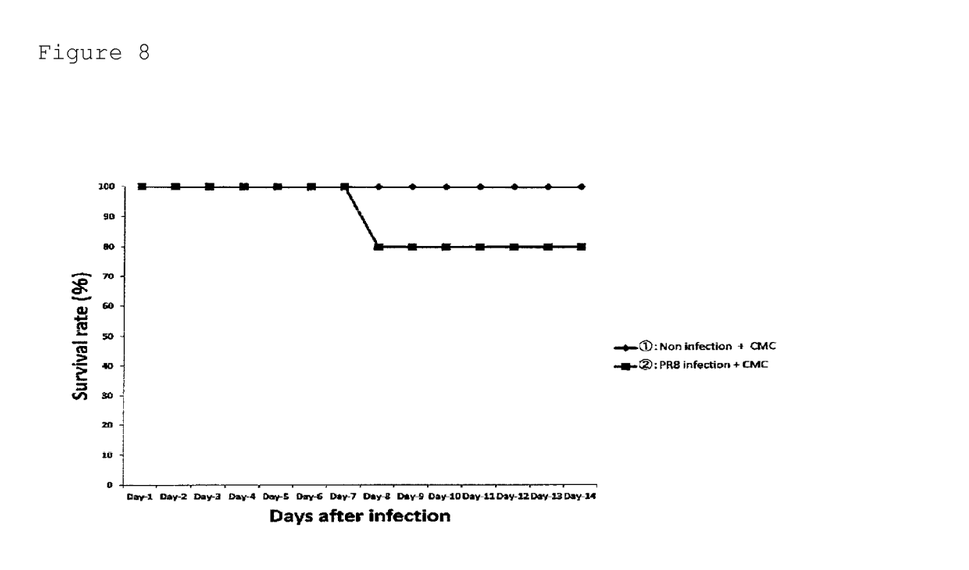
FIG. 8 is a diagram illustrating transition of a survival rate obtained in administering 5-ALA and sodium ferrous citrate of the present invention to model mice for aggravation of influenza.

The transition of the survival rate is illustrated in FIG. 8. In the case of infection with a viral load of 100 PFU, a fatal case appeared on Day-8 in the group 2) infected with the virus, but a survival rate of 80% was kept thereafter. When the result of the survival rate of this reference example (that is, a survival rate of 80% on Day-14) is compared with the result of the survival rate attained in the case where the influenza virus PR8 strain of Example 2 was used (that is, a survival rate of 0% on Day-14; see FIG. 5), it is understood that the influenza virus PR8 strain of Example 2 shows a higher fatality rate. This reveals that the survival rate could be recovered to be as high as 30% in the group 3) infected with the virus (100 PFU) and administered with ALA+Fe even when the influenza virus PR8 strain of Example 2 showing a high fatality rate was used (see FIG. 5).

INDUSTRIAL APPLICABILITY

The prophylactic/therapeutic agent for influenza viral infection of the present invention can be advantageously used in the medical field.

The invention claimed is:

1. A method for ameliorating: depression in food consumption, water consumption and/or body weight; increase in ketone body levels in blood; depression in ATP levels in blood; survival rate; and/or abnormality in a body surface temperature in a subject having an influenza viral infection, comprising administering to the subject a therapeutic agent for influenza viral infection comprising a compound represented by formula (I) or a salt thereof:

(I)

(wherein $R^1$ represents a hydrogen atom or an acyl group, and $R^2$ represents a hydrogen atom, a linear or branched alkyl group, a cycloalkyl group, an aryl group or an aralkyl group).

2. The method according to claim 1, wherein $R^1$ and $R^2$ represent a hydrogen atom.

3. The method according to claim 1, wherein the therapeutic agent for influenza viral infection further comprises an iron compound.

4. The method according to claim 3, wherein the iron compound is one or more compounds selected from ferric chloride, iron sesquioxide, iron sulfate, ferrous pyrophosphate, ferrous citrate, iron sodium citrate, sodium ferrous citrate, iron ammonium citrate, ferric pyrophosphate, iron lactate, ferrous gluconate, iron sodium diethylenetriaminepentaacetate, iron ammonium diethylenetriaminepentaacetate, iron sodium ethylenediamine tetraacetate, iron ammonium ethylenediamine tetraacetate, iron sodium dicarboxymethylglutamate, iron ammonium dicarboxymethylglutamate, ferrous fumarate, iron acetate, iron oxalate, ferrous succinate, sodium iron succinate citrate, heme iron, iron dextran, iron triethylenetetramine, lactoferrin iron, transferrin iron, sodium iron chlorophyllin, ferritin iron, saccharated iron oxide and iron glycine sulfide.

5. The method according to claim 4, wherein the iron compound is sodium ferrous citrate.

6. The method according to claim 2, wherein the therapeutic agent for influenza viral infection further comprises an iron compound.

7. The method according to claim 6, wherein the iron compound is one or more compounds selected from ferric chloride, iron sesquioxide, iron sulfate, ferrous pyrophosphate, ferrous citrate, iron sodium citrate, sodium ferrous citrate, iron ammonium citrate, ferric pyrophosphate, iron lactate, ferrous gluconate, iron sodium diethylenetriaminepentaacetate, iron ammonium diethylenetriaminepentaacetate, iron sodium ethylenediamine tetraacetate, iron ammonium ethylenediamine tetraacetate, iron sodium dicarboxymethylglutamate, iron ammonium dicarboxymethylglutamate, ferrous fumarate, iron acetate, iron oxalate, ferrous succinate, sodium iron succinate citrate, heme iron, iron dextran, iron triethylenetetramine, lactoferrin iron, transferrin iron, sodium iron chlorophyllin, ferritin iron, saccharated iron oxide and iron glycine sulfide.

8. The method according to claim 7, wherein the iron compound is sodium ferrous citrate.

\* \* \* \* \*